United States Patent
Briggs et al.

(10) Patent No.: US 9,174,905 B2
(45) Date of Patent: *Nov. 3, 2015

(54) PROCESS FOR TELOMERIZATION OF BUTADIENE USING A MONO-ORTHOALKOXY SUBSTITUTED CATALYST

(75) Inventors: John R. Briggs, Midland, MI (US); Jasson T. Patton, Midland, MI (US); Daryoosh Beigzadeh, Midland, MI (US); Peter M. Margl, Midland, MI (US); Henk Hagen, Terneuzen (NL); Sonet Vermaire-Louw, Vlissingen (NL)

(73) Assignee: Dow Global Technologies LLC, Midland, MI (US)

( * ) Notice: Subject to any disclaimer, the term of this patent is extended or adjusted under 35 U.S.C. 154(b) by 124 days.

This patent is subject to a terminal disclaimer.

(21) Appl. No.: 13/883,688

(22) PCT Filed: Dec. 14, 2011

(86) PCT No.: PCT/US2011/064764
§ 371 (c)(1),
(2), (4) Date: May 6, 2013

(87) PCT Pub. No.: WO2012/087686
PCT Pub. Date: Jun. 28, 2012

(65) Prior Publication Data
US 2013/0261342 A1    Oct. 3, 2013

Related U.S. Application Data

(60) Provisional application No. 61/425,373, filed on Dec. 21, 2010.

(51) Int. Cl.
| | |
|---|---|
| *C07F 9/50* | (2006.01) |
| *C07C 41/06* | (2006.01) |
| *C07C 1/20* | (2006.01) |
| *C07C 41/20* | (2006.01) |

(52) U.S. Cl.
CPC . *C07C 41/06* (2013.01); *C07C 1/20* (2013.01); *C07C 41/20* (2013.01); *C07F 9/5022* (2013.01)

(58) Field of Classification Search
USPC .............................. 568/13, 15, 17
See application file for complete search history.

(56) References Cited

U.S. PATENT DOCUMENTS

| | | |
|---|---|---|
| 5,254,782 A | 10/1993 | Schaart et al. |
| 6,153,780 A | 11/2000 | Traenckner et al. |
| 6,310,259 B1 | 10/2001 | Keim et al. |
| 7,115,790 B2 | 10/2006 | Beller et al. |
| 7,141,539 B2 | 11/2006 | Edwards |
| 2005/0038305 A1 | 2/2005 | Edwards |

FOREIGN PATENT DOCUMENTS

WO    2010/019360 A2    2/2010

OTHER PUBLICATIONS

Vollmuller; European Journal of inorganic Chemistry, 2000, 1825-1832.*
Maddock, et al., "Palladium-Catalyzed Head-to-Head Telomerization of Isoprene with Amines" Organometallics, 2000, pp. 2684, 19.
Prinz, T., et al., "Biphasic Catalyzed Telomerization of Butadiene and Ammonia: Kinetics and New Ligands for Regioselective Reactions" Chem. Eur. J. 1999, pp. 2069-2076, 5, No. 7, Wiley-VCH, Verlag GmbH.
Tolman, C. A., "Steric Effects of Phosphorus Ligands in Organometallic Chemistry and Homogeneous Catalysis," Chem. Rev. 1977, 77, No. 3, 313-348.
Benvenuti, et al., "Telomerization of 1, 3-butadiene with alcohols catalyzed by homogeneous palladium(0) complexes in the presence of mono- and diphosphine ligands" J of Molecular Catalysis A: Chemical, 1999 pp. 27-40, 144, XP002675409.
Van Leeuwen, P., "Homogeneous Catalysis—Understanding the Art," 2004, pp. 11-12 Kluwer Academic Publishers, Dordrecht—Netherlands, XP002675358.
PCT/2011/064764, International Search Report and Written Opinion, May 23, 2012.
PCT/2011/064764, International Preliminary Report on Patentability, Mar. 18, 2013.

* cited by examiner

*Primary Examiner* — Sudhakar Katakam
*Assistant Examiner* — Pancham Bakshi

(57) ABSTRACT

A process for the telomerization of butadiene comprises reacting 1,3-butadiene and an alkanol, in the presence of a catalyst promoter and an alkoxydimerization catalyst comprising a Group VIII transition metal and a triarylphosphine ligand, which includes one phenyl that is mono-ortho-alkoxy substituted and at least one other phenyl including at least one substituent that withdraws electrons from the phosphorus atom. The product includes an alkoxy-substituted octadiene, which may then be used to produce 1-octene. The catalyst shows improved stability, activity and selectivity toward the alkoxy-substituted octadiene.

9 Claims, No Drawings

PROCESS FOR TELOMERIZATION OF BUTADIENE USING A MONO-ORTHOALKOXY SUBSTITUTED CATALYST

This application is a non-provisional application claiming priority from the U.S. Provisional Patent Application No. 61/425,373, filed on Dec. 21, 2010, entitled "PROCESS FOR TELOMERIZATION OF BUTADIENE USING A MONO-ORTHOALKOXY SUBSTITUTED CATALYST" the teachings of which are incorporated by reference herein, as if reproduced in full hereinbelow.

BACKGROUND

1. Field of the Invention

This invention relates to a process for the telomerization of conjugated dienes. More particularly, it relates to a process wherein 1,3-butadiene is alkoxydimerized in the presence of a catalyst containing a noble metal and a triarylphosphine ligand that contains only one ortho-alkoxy group and also contains at least one electron-withdrawing group, which shows desirable stability and selectivity toward the 1-alkoxy octadiene product.

2. Background of the Art

A highly useful chemical for a variety of purposes, 1-octene is produced in various locations throughout the world. It is used, in particular, as a co-monomer in production of polyethylene, and as a starting material to produce linear aldehyde, via an oxo synthesis (hydroformylation), which is in turn used to produce the plasticizer nonanoic acid. The 1-octene may be produced by, for example, the oligomerization of ethylene or by a Fischer-Tropsch synthesis, but an increasingly valuable method is via the telomerization of butadiene. This telomerization reaction involves the oligomerization, and particularly the dimerization, of butadiene with the concomitant addition of a nucleophilic agent. Examples of such agents include compounds containing one or more active hydrogen atoms, such as water, alcohols and amines. The nucleophile is introduced primarily at the terminal position of the oligomer, and especially of the dimer, of the butadiene.

Telomerization reactions catalyzed by Group VIII transition metal catalysts are described extensively in the prior art. Historically, attention was focused primarily on optimization of conversion and selectivity of the telomerization reaction under batch conditions, but eventually focus changed to more easily enable continuous production methods. A focus on catalyst selection led, for economic reasons, to the evolution of processes enabling catalyst reuse. Such often required techniques to separate the catalyst from the product mixture, by means including, for example, distillation, precipitation and/or extraction. Care was required to avoid catalyst decomposition or metallization, which could then require an additional catalyst regeneration step.

Despite the many processes and catalysts that have been identified, such processes continue to produce a variety of products, and selectivity particularly to the product required for production of 1-octene i.e., 1-methoxy-2,7-octadiene (OD-1-R), is generally less than desirable. Accordingly, processes that enhance selectivity to OD-1-R, and that reduce problems such as catalyst instability, continue to be sought.

SUMMARY OF THE INVENTION

In one aspect the invention provides a process for the telomerization of butadiene comprising reacting, in a reaction zone in the liquid phase, 1,3-butadiene and an active hydrogen containing compound, in the presence of a catalyst that includes a Group VIII transition metal and a phosphine ligand having three phenyl groups, wherein one phenyl group includes as a substituent exactly one ortho-alkoxy group, and at least one of the other two phenyl groups each includes at least one substituent that has a Hammett constant value greater than zero, such that the phosphine ligand has a Tolman's chi value ranging from 10 to 18, and a catalyst promoter; under conditions such that a reaction product including at least one alkoxy-substituted octadiene is formed.

In another aspect the invention provides a process for producing 1-octene from butadiene, comprising (1) reacting 1,3-butadiene and an active hydrogen containing compound, in the presence of an alkoxydimerization catalyst including a Group VIII transition metal and a phosphine ligand having three phenyl groups, wherein one phenyl group includes as a substituent exactly one ortho-alkoxy group, and at least one of the other two phenyl groups includes at least one substituent that has a Hammett constant value greater than zero, such that the phosphine ligand has a Tolman's chi value ranging from 10 to 18, and a catalyst promoter; under conditions suitable to form an alkoxy-substituted octadiene; (2) hydrogenating the alkoxy-substituted octadiene under conditions suitable to form an alkoxy-substituted octane; and (3) decomposing the alkoxy substituted octane under conditions suitable to form 1-octene.

In another aspect the invention provides a composition of matter comprising bis(4-chlorophenyl)(2-methoxyphenyl)phosphine, bis(4-fluorophenyl)(2-methoxyphenyl)phosphine, or a combination thereof.

DETAILED DESCRIPTION OF THE EMBODIMENTS

The present invention provides a process for producing 1-octene from 1,3-butadiene. This process generally includes a combined dimerization and alkoxy-substitution of the diolefin to produce an alkoxy-substituted octadiene (preferably methoxy-substituted octadiene); hydrogenation of the alkoxy substituted octadiene to form an alkoxylated octane (preferably methoxylated octane); and elimination of the alkoxy group to produce the corresponding alkanol (preferably methanol) and the target 1-octene. This process is economically attractive because conversion efficiency is high, the butadiene and alkanol are relatively inexpensive starting materials, and the phosphine ligands described herein show both enhanced selectivity to the desired 1-alkoxy substituted octadiene in the alkoxydimerization product, and improved stability, in comparison with some other phosphine-based alkoxydimerization ligands employed in a similar reaction scheme.

For the alkoxydimerization reaction the general reaction scheme is as follows:

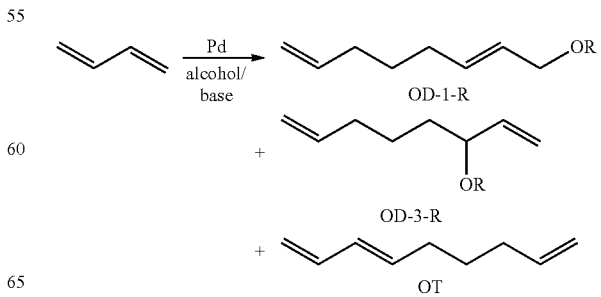

The OD-1-R fraction of the alkoxydimerization product, 1-alkoxy-2,7-octadiene, is the fraction that may then be hydrogenated to form a hydrogenation product, particularly the 1-alkoxy substituted octane fraction thereof. This 1-alkoxy substituted octane may then be eliminated to form 1-octene. In view of this, selectivity to the OD-1-R fraction is desirable for the alkoxydimerization. The OD-3-R fraction of the telomerization product is more specifically 3-alkoxy-1,7-octadiene and the fraction designated as "octatriene" in the schematic (OT) is, to be more specific, 1,3,7-octatriene.

The first reactant for the alkoxydimerization is an active hydrogen containing compound. In certain particular and preferred embodiments the active hydrogen containing compound is an alkanol, shown in the reaction scheme by the more common name "alcohol," but in less preferred embodiments it may be selected from water, a carboxylic acid, an amine, a polyol, or a combination thereof. Where the preferred alkanol is selected, it desirably has from 1 to 10 carbon atoms, more preferably 1 to 3 carbon atoms and is suitable to serve as both a solvent and a reactant. Particularly preferred is methanol, but ethanol or propanol may also be desirably selected. For convenience herein, the term alkanol will be used hereinafter to represent the active hydrogen containing compounds in general, including but not limited to true alkanols.

As will be noted from the reaction scheme hereinabove, the alkoxy-dimerization is carried out in the presence of a catalyst. This catalyst comprises two parts: One part is a Group VIII transition metal-containing compound, and the other part is a specific phosphine ligand, both aspects of which are further described hereinbelow.

The first part of the catalyst used in the present invention is selected from Group VIII transition metals, i.e., "noble" metals. Such may include palladium (Pd), platinum (Pt), iridium (Ir), rhenium (Re), ruthenium (Ru), osmium (Os), and combinations thereof. In certain embodiments Pd, Pt, and Ru are preferred, and Pd is more preferred, and is included for illustration only in the reaction schematic hereinabove. This is most conveniently employed in the form of a salt, preferably a soluble or superficially insoluble salt with respect to the alkanol (which may also include, as a mixture, the ligand, which is discussed in detail hereinbelow) into which it is to be incorporated. By "superficially insoluble" is meant that the alkoxydimerization catalyst comprises salt(s) which appear to be insoluble in the alkanol or alkanol-ligand mixture, but which appear to produce "noble metal moieties" which are catalytically effective.

Without wishing to be bound by any particular theory, the chemical transformations that involve the alkoxydimerization catalyst are quite complex, probably involving the formation and destruction of complexes between the noble metal salt or noble metal moieties, the butadiene, any ligand included, and/or the presumed butadiene dimer intermediate. The formation of catalytically effective noble metal moieties is believed to be influenced by interaction of the alkoxydimerization catalyst with the butadiene, the presumed butadiene dimers, and/or the alkanol. To obtain optimum reaction rates, the alkoxydimerization catalyst preferably includes an alkanol-soluble noble metal salt.

Suitable, non-limiting salts of the noble metal may be organic or inorganic acids. Illustrative examples include the halide and carboxylate salts. Acetylacetonate salts, such as Pd acetylacetonate ($Pd(AcAc)_2$), may also be useful. Also suitable are salts wherein the noble metal is present in an anion, such as, for example, chloropalladate or chloroplatinate salts. Metal complexes are also suitable, such as metal complexes with tertiary nitrogen-containing ligands. The known Pd allyl complexes are also suitable. Less preferred alkoxydimerization catalysts may comprise two noble metal atoms per molecule. Such alkoxydimerization catalysts may include, but are not necessarily limited to, tris(dibenzylideneacetone)di noble metal. A preferred alkoxydimerization catalyst is tris (dibenzylideneacetone)di-palladium. The alkoxy-dimerization catalyst may be provided fresh and/or as a recycled stream from the alkoxydimerization (i.e., the telomerization) process.

The alkoxydimerization catalyst further includes a phosphine ligand. The phosphine ligands used in the present invention are newly identified as enabling significantly improved selectivity and improved activity to the alkoxy substituted octadienes in the alkoxydimerization product, and particularly to the 1-alkoxy substituted octadiene, and also significantly improved stability at high methanol concentrations, for example, greater than 10.4 molar (M), in comparison with some other triarylphosphine ligands. The selected ligand is desirably a phosphine ligand having three phenyl groups, i.e., a triarylphosphine, wherein one phenyl group includes as a substituent an ortho-alkoxy group, and the other two phenyl groups each include as a substituent an electron-withdrawing moiety that is not an ortho-alkoxy group. As defined herein, the electron-withdrawing substituent(s) may be any that withdraws electron density from the phosphorus atom, and can be identified as having a positive Hammett constant value, denoted as $\sigma_m$ or $\sigma_p$ (when positioned at the meta or para position, respectively, in relation to the phosphorus atom), and may therefore be selected from the group consisting of fluoride, chloride, bromide, iodide, nitro, organic functions such as aldehyde, carboxylic acid, ester, ketone, cyanide, any other group that has a Hammett constant greater than zero, and combinations thereof. In preferred embodiments, the electron-withdrawing substituent is selected from trifluoromethyl, fluoride, chloride, and combinations thereof, and more preferred are fluoride, chloride and combinations thereof.

Overall, the ligand desirably meets the Tolman's chi parameter value for phosphine basicity. This means that the ligand's estimated chi value, obtained by Tolman's method (see, e.g., Tolman, C. A., "Steric Effects of Phosphorus Ligands in Organometallic Chemistry and Homogeneous Catalysis," Chem. Rev. 1977, 77, 313-348, p. 313) lies in a range from 10 to 18, more preferably from 10 to 16, and most preferably from 10 to 14. Possible ligands thus may include, in non-limiting example, those corresponding the chemical structures designated as structures "3," and "4" in the "Chi Values Chart" hereinbelow.

Chi Values Chart

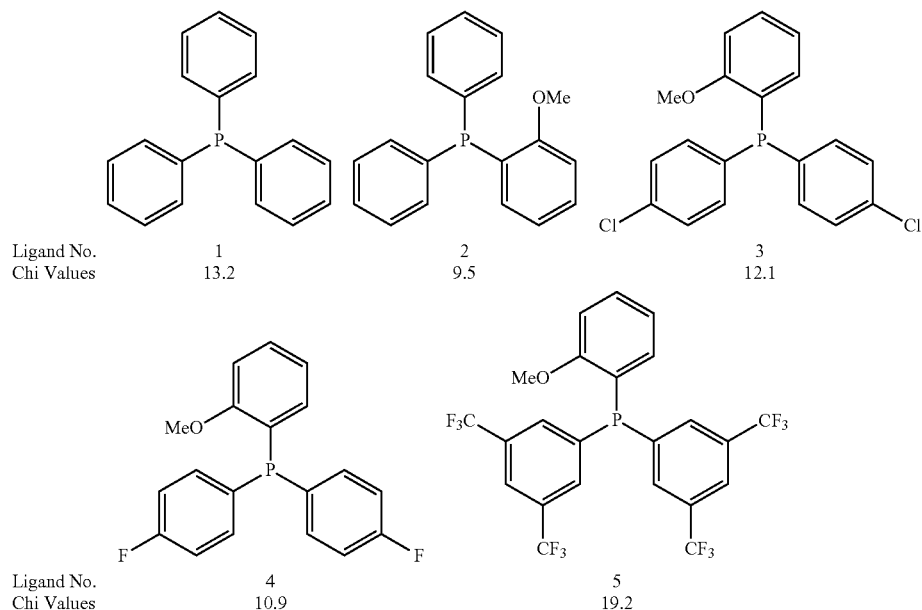

| Ligand No. | 1 | 2 | 3 |
|---|---|---|---|
| Chi Values | 13.2 | 9.5 | 12.1 |

| Ligand No. | 4 | 5 |
|---|---|---|
| Chi Values | 10.9 | 19.2 |

The amount of each aspect of the catalyst to the other aspect is important. In particular embodiments the molar ratio of the defined phosphine ligand to the Group VIII transition metal compound preferably ranges from 0.5:1 to 4:1. In more preferred embodiments it ranges from 1:1 to 3:1. Most preferably it ranges from 1.5:1 to 2.5:1. The catalyst, including the two components, is desirably employed in an amount that is sufficient to produce the desired alkoxydimerization, preferably representing an amount of the noble metal ranging from 0.005 mole % to 0.1 mole %, more preferably from 0.01 mole % to 0.05 mole %, based on the total reactants.

A catalyst promoter may also be included in the inventive process. When a palladium(II) compound, for example, is used as the catalyst precursor, it generally takes a certain period of time to form an active catalyst under the reaction conditions. This time period, which is dependent on electronic and steric properties of the phosphine ligand, is referred to as the induction period. The induction period is generally more than one (1) minute, but less than two (2) hours. The catalyst promoter is advantageously employed to shorten or essentially eliminate the induction period.

The catalyst promoter may be selected from the group consisting of tertiary amines, alkali metal borohydrides, oxides, and compounds having a generic formula $(RO^-)_n M^{n+}$, wherein R is hydrogen, a $C_1$-$C_{20}$ hydrocarbyl, or a substituted $C_1$-$C_{20}$ hydrocarbyl, M is an alkali metal, alkaline earth metal or quaternary ammonium, and n is 1 or 2. More preferably, the catalyst promoter is selected from compounds having a generic formula $RO^-M$, wherein $RO^-$ is derived from the organic alkanol and M is lithium, sodium or potassium.

In addition to reducing or essentially eliminating the induction period, a promoter may also increase the efficiency of the palladium catalyst. Without wishing to be bound by any exact theory or mechanistic discourse, the promoter employed in the process advantageously is sufficiently basic in nature to deprotonate at least a fraction of the organic hydroxyl compound (the alkanol), which is believed to increase the rate of the telomerization reaction.

The process preferably employs an amount of the catalyst promoter, dependent upon its properties, such as basicity and solubility in the reaction fluid, sufficient to shorten or essentially eliminate the induction period. Thus, it is desirable that the molar ratio of the catalyst promoter to the palladium (or other noble metal) ranges from 1:1 to 1000:1; more preferably from 1:1 to 100:1; and most preferably from 2:1 to 20:1.

In order to perform the alkoxydimerization reaction, it is usual to first prepare the catalyst mixture and expose it to "activation conditions." Such conditions are defined as those effective to (a) dissolve any reactants other than the alkoxydimerization catalyst, and (b) to activate the alkoxydimerization catalyst. The result is an activated catalyst mixture. The activation conditions comprise maintaining the alkoxydimerization catalyst mixture at an activation temperature for a period of time effective to activate the catalyst (referred to as the activation time). If the alkoxydimerization catalyst includes an alkanol soluble noble metal salt, then the activation temperature and the activation time are effective to dissolve the noble metal salt in the alkanol/ligand solution. If the alkoxydimerization catalyst is superficially alkanol insoluble, then the activation temperature and activation time are effective to liberate "noble metal compound moieties" in the alkanol/ligand solution.

As the term is used herein, "butadiene" means specifically 1,3-butadiene, which is preferably added to the activated catalyst mixture. The butadiene may be obtained from any known source. A particularly advantageous source of butadiene is crude C4. The amount of butadiene added is preferably effective to produce an optimum butadiene:alkanol mole ratio. This ratio depends in part upon the specific alkanol and the desired conversion. A butadiene:alkanol mole ratio of as low as 1:5 is suitable where low conversion is desired or acceptable. To obtain higher conversion, a more substantial proportion of butadiene is preferred and the butadiene:alkanol mole ratio may range from 1:3 to 1:0.5. Most preferably the butadiene:alkanol mole ratio ranges from 1:2 to 1:1.

It is possible to use solvents in addition to the alkanol in the reaction mixture, provided that such additional solvents are inert to the reaction. However, such is not preferred. Where another solvent is deemed desirable, suitable selections include those listed hereinbelow as suitable for hydrogenation.

It is also preferred that the reaction of the butadiene and the alkanol be carried out in the presence of a basic promoter, which is generalized as "base" in the schematic hereinabove. This basic promoter is sufficiently basic to deprotonate at least a fraction of the alkanol, e.g. methanol, and increase the rate of the telomerization reaction. The basic promoter may be, in non-limiting example, sodium hydroxide, sodium methoxide, any of the potential catalyst promoter selections provided hereinabove, or a combination thereof. Preferred is sodium hydroxide or sodium methoxide.

When the butadiene is added to the activated catalyst mixture, which represents a preferred embodiment, the result is an exothermic reaction. In order to counter this and ensure adequate temperature control, it may be desirable under laboratory scale conditions to cool the activated catalyst mixture prior to adding the butadiene, though such may be unnecessary at commercial scale. At laboratory scale it may therefore be preferred that the activated catalyst mixture be cooled to a temperature below 70° C., and more preferably to approximately 60° C. The combined activated catalyst mixture and butadiene comprises the alkoxydimerization mixture.

This alkoxydimerization mixture may then be slowly heated to a preliminary temperature equal to or less than 120° C., preferably equal to or less than 60° C., preferably with agitation. Thereafter the alkoxydimerization mixture may be heated to and maintained at an alkoxydimerization temperature that is effective to produce at least 90 wt % of the 1-alkoxy substituted octadiene, i.e., the OD-1-R, based on butadiene consumed. A preferred alkoxydimerization temperature ranges from 40° C. to 130° C., more preferably 50° C. to 120° C., still more preferably 60° C. to 100° C., and most preferably from 60° C. to 90° C. The alkoxydimerization temperature is maintained for an alkoxydimerization time of at least 2 hours, preferable from 2 hours to 8 hours, more preferably from 2 hours to 6 hours, and most preferably about 4 hours.

Typical alkoxydimerization pressures may vary from 5 atm to 30 atm (~0.51 MPa to ~3.04 MPa). Frequently good results may be obtained when the alkoxydimer-ization pressure is autogenous, or when the alkoxydimerization pressure is the pressure generated when the reactants are maintained at the alkoxydimerization temperature in a sealed reaction vessel. Such pressures are from 1 atm to 30 atm (~0.01 MPa to ~3.04 MPa).

Once the alkoxydimerization time has passed, the mixture is cooled, preferably to the preliminary temperature, which is desirably equal to or less than 25° C. The cooled product is depressurized and may be fed directly to the hydrogenation, or the alkoxylated octadienes may be first recovered and then fed to hydrogenation. Recovery of the alkoxylated octadienes is accomplished using any suitable means, such as selective extraction, fractional distillation, and chromatographic techniques. In preferred embodiments the product of the alkoxydimerization is at least 90 weight percent (wt %) of the desired 1-alkoxy substituted octadiene, and preferably at least 93 wt %, and most preferably at least 95 wt %.

The 1-alkoxy substituted octadiene prepared hereinabove may be hydrogenated to form an alkoxylated octane. Because the alkoxydimerization catalyst includes a noble metal, the hydrogenation may be carried out using the alkoxydimerization catalyst. However, greater efficiency may be achieved when the alkoxydimerization product is separated and fed to a hydrogenation reactor comprising a fixed bed hydrogenation catalyst. Substantially any of the known heterogeneous or homogeneous hydrogenation catalysts may be used. Preferred hydrogenation catalysts are heterogeneous.

Suitable hydrogenation catalysts comprise a metal having an atomic number from 26 to 78, which includes but is not necessarily limited to Fe, Co, Ni, Cu, Zn, Ga, Ge, As, Se, Br, Kr, Rb, Sr, Y, Zr, Nb, Mo, Tc, Ru, Rh, Pd, Ag, Cd, In, Sn, Sb, te, I, Xe, Cs, Ba, the lanthanide series (comprising Ce, Pr, Nd, Pm, Sm, Eu, Gd, Tb, Dy, No, Er, Tm, Yb, Lu), Hf, Ta, W, Re, Os, Ir, and Pt. Preferred metals for the hydrogenation catalyst have an atomic number of 28 to 78, thereby comprising the above list excluding Fe and Co. Other known catalysts suitable for hydrogenation include the oxides and sulfides of Group VI, including but not limited to Cr, Mo and W.

The hydrogen may be provided as pure hydrogen gas ($H_2$) or may be diluted with one or more additional gases. Suitable diluent gases are inert, and do not interfere with the hydrogenation process. For example, it may be desirable to use a process gas, such as syngas, to supply the required hydrogen. Such a process gas is suitable for use as the hydrogen source provided the process gas does not interfere with the hydrogenation process.

The hydrogenation may be carried out either as a batch process or as a continuous process, and such is preferably continuous. In a batch process, a homogeneous or heterogeneous catalyst is charged to the reactor along with the reactants, and the reactor is pressured with hydrogen or a hydrogen-containing gas. In a continuous process the hydrogenation catalyst preferably is a solid comprised in a packed bed, more preferably a supported metal catalyst, and the alkoxy substituted octadiene(s) and hydrogen are simultaneously passed through the bed, which is maintained at hydrogenation conditions.

In general any conventional hydrogenation process can be used. The hydrogenation may be carried out in the liquid phase, or in the vapor phase. Depending on the nature of the starting material, the reaction can be carried out at a temperature from 0° C. to 400° C. Preferably, the temperature ranges from ambient to 350° C. More preferably the hydrogenation is carried out at a temperature from 50° C. to 200° C. The pressure is not critical and depends on whether the hydrogenation is carried out in the liquid or in the vapor phase. In general the pressure can vary from 0.1 to 100 bar (10 kilopascals (kPa) to 10,000 kPa).

The hydrogenation may be carried out either in the presence or absence of a solvent. If a solvent is used, such is preferably inert to the hydrogenation conditions and reactants. Suitable solvents may include, but are not necessarily limited to, ethers, aromatic hydrocarbons, paraffins, halogenated hydrocarbons, nitriles, and combinations thereof.

By way of example, suitable ethers may include dialkyl ethers, alkyl aryl ethers, cyclic ethers, and lower alkyl ethers. Examples of specific ethers include but are not necessarily limited to dibutyl ether, methyl hexyl ether, anisole, phenyl butyl ether, tetrahydrofuran, dioxane, dioxolane, ethylene glycol dimethyl ether, diethylene glycol dimethyl ether, tetraethylene glycol dimethyl ether, and glycol triethyl ether. Suitable aromatic hydrocarbons may include benzene, toluene, and xylene. Suitable halogenated hydrocarbons may include chloroform, carbon tetrachloride, tetrachloroethylene, methylene chloride, and bromoform. Suitable sulfoxides may include, for example, dimethylsulfoxide. Suitable nitriles may include acetonitrile and benzonitrile.

The result of the hydrogenation step is an alkoxylated octane. This alkoxylated octane may then be subjected to decomposition conditions suitable to both eliminate the alkoxy group in the form of an alkanol, and also to produce the 1-octene that is frequently a desirable ultimate target product. This decomposition is technically an ether cleavage, wherein, for example, methyloctylether (the alkoxylated octane) undergoes ether cleavage to yield 1-octene and an alkanol, for example, methanol. Although this decomposition may be carried out in the absence of a suitable catalyst, it is preferred to use a catalyst in order to increase the yield of 1-octene. A solid acid catalyst, preferably an alumina catalyst, may be effective for this purpose. Examples of such catalysts may include alpha, delta, gamma, eta and theta aluminas, which may be modified by bases such as sodium hydroxide, or by other treating agents. In certain particular embodiments gamma alumina is employed.

The temperature at which the decomposition is carried out depend on both the catalyst activity and the decomposition temperature of the respective compound being decomposed. In particular embodiments, for example, where the compound being decomposed is methyloctylether, the decomposition temperature may range from 200° C. to 500° C., preferably from 200° C. to 400° C., and more preferably from 250° C. to 350° C. The pressure under which the decomposition reaction may be carried out can also vary widely, but is preferably maintained from 1 to 2 bar (100 kPa to 200 kPa) in order to ensure high activity.

The final step be carried out in the vapor or the liquid phase, the vapor phase being frequently preferred. An inert gas or an inert liquid diluent may be used to dilute the material being decomposed, for example, methyloctylether. Examples of such inert gases may include nitrogen, helium, argon, and combinations thereof. Alternatively, another ether may be used as a diluent. When employed, the diluent is desirably in a weight ratio, diluent-to-reactant, ranging from greater than 0:1 to 100:1, and preferably from 1:1 to 20:1. Selection of an ether as a diluent may offer some advantage by enabling recycle, which may in turn help to reduce net alcohol loss. For instance, where methyloctylether is selected as a reagent, some methanol will be produced in the decomposition reaction. This methanol then dehydrates to form dimethylether (DME) and water, and this reaction occurs simultaneously with the ether cleavage reaction to yield 1-octene and methanol. If the produced DME is then recycled back to the decomposition reactor, water may then also be added, which will help to ensure that there is no net alcohol loss across the process. The produced methanol can also be recycled, back to the first process step.

The decomposition reaction may be carried out continuously, semi-continuously or batchwise. In the continuous mode the reactant(s) and, where used, any diluent(s) may be passed continuously over a catalyst bed under the desired reaction conditions. The reactant(s) may be added to the reactor at a weight hourly space velocity (WHSV) ranging from 0.01 gram of 1-substituted octane per gram catalyst per hour (g/g cat/h) to 50 g/g cat/h, preferably from 0.1 g/g cat/h to 10 g/g cat/h.

The decomposition step may, in another aspect, be carried out isothermally or, alternatively, adiabatically. In the case of a fixed bed adiabatic operation, the temperature in the reactor will generally drop over reactor length, due to the endothermic nature of the decomposition reaction. The exit temperature of the reactor should desirably remain above the dew point of the effluent mixture, in order to reduce or avoid condensation of liquids onto the catalyst. The initial inlet temperature and the extent of the temperature drop correlate to the level of conversion of the 1-substituted octane to 1-octene and also to the ratio of diluent to reactant, i.e., a greater temperature drop indicates a higher conversion level, and a higher diluent-to-reactant ratio tends to lead to a higher conversion level at a given inlet temperature. In preferred embodiments the molar conversion of 1-substituted octane to 1-octene may range from 40 to 80 percent of theoretical, based on the inlet concentration of the 1-substituted octane.

EXAMPLES

Experimental

Anhydrous methylcyclohexane (MCH) and methanol ($CH_3OH$) purchased from Aldrich are purified by passing through activated alumina in a glovebox. Dibutyl ether (gas chromatography internal standard, purchased from Aldrich, is stirred over a sodium/potassium alloy overnight, then filtered through activated alumina. Phosphines designated in the Chi Values Chart hereinabove as Ligands 1 and 2, (4-chlorophenyl)magnesium bromide (1.0 M solution in diethylether), (4-fluorophenyl)magnesium bromide (2.0 M solution in diethylether), (3,5-bis-trifluoromethylphenyl)magnesium bromide (1.0 M solution in diethylether), and n-butyllithium (n-BuLi) (2.0 M solution in cyclohexane), are used as purchased from Aldrich.

Example 1

Preparation of
Bis(4-chlorophenyl)(2-methoxyphenyl)phosphine,
*Ligand 3 (*See Chi Values Chart Hereinabove)

To a stirred solution of dimethyl 2-methoxyphenylphosphonite (1.0 g, 5.0 mmol) in diethyl ether (40 mL) at 0° C. is added dropwise over 30 minutes a solution (1 M) of (4-chlorophenyl)magnesium bromide in diethyl ether (10.5 mL, 10.5 mmol). After allowing to warm to room temperature, the mixture is filtered and stripped to give an oil that is triturated with MeOH to give a white solid (0.98 g, 58%) $^1H$ NMR ($C_6D_6$): δ 7.09 (m, 5H), 7.03 (m, 4H), 6.78 (m, 1H), 6.74 (m, 1H), 6.47 (d of d, 1H, J=8.2, 4.7), 3.16 (s, 3H); $^{13}C$ NMR ($C_6D_6$): δ 161.47 (d, 1C, $J_{CP}$=15.1 Hz), 135.88 (d, 2C, $J_{CP}$=13.8 Hz), 135.52 (d, 4C, $J_{CP}$=21.4), 135.30 (s, 2C), 133.74 (d, 1C, $J_{CP}$=2.6 Hz), 130.86 (s, 1C), 128.99 (d, 4C, $J_{CP}$=6.6 Hz), 125.60 (d, 1C, $J_{CP}$=14.2 Hz), 121.47 (s, 1C), 110.64 (s, 1C), 55.15 (s, 1C); $^{31}P$ NMR ($C_6D_6$) δ-16.54. Elemental analysis calculated for $C_{19}H_{15}Cl_2OP$: C, 63.18; H, 4.19; 0, 4.43; P, 8.58. Measured: C, 63.31; H, 4.40.

Example 2

Preparation of
Bis(4-fluorophenyl)(2-methoxyphenyl), *Ligand 4

To a stirred solution of dichloro(2-methoxyphenyl)phosphine (1.50 g, 7.18 mmol), in tetrahydrofuran (50 mL), cooled to 0° C. is added a diethyl ether solution of (4-fluorophenyl)magnesium bromide (2 M, 7.18 mL, 14.4 mmol) dropwise over a 30 minute period. This mixture is allowed to warm to room temperature and then refluxed overnight to give a precipitate which is filtered off. The filtrate is concentrated in vacuo, resulting in a brown viscous oil which is extracted with warm toluene. The toluene solution is washed with degassed de-ionized water and brine. The top organic layer is dried over $MgSO_4$, filtered and dried in vacuo yielding a viscous yellow oil. Crystallization from hexane at −35° C. gives 0.490 g (21%) of the desired product. $^1H$ NMR ($C_6D_6$): δ 7.21-7.09 (m, 5H), 6.83-6.69 (m, 6H), 6.52-6.48 (m, 1H), 3.18 (s, 3H); $^{13}C$ NMR ($C_6D_6$): δ 165.32 (s), 162.03 (s), 161.37 (d, J=15.2), 136.13 (dd, J=22.3, 8.0), 133.62 (d, J=1.8), 133.04 (dd, J=12.7, 3.6), 130.65 (s), 121.40 (s), 115.84 (dd, J=20.6, 7.7), 110.64 (d, 1.5), 55.26 (s); $^{31}$P NMR ($C_6D_6$): δ (externally referenced with neat $H_3PO_4$): −17.12 (t, J=4.9); $^{19}$F NMR ($C_6D_6$): δ (externally referenced with neat $CCl_3F$): −133.00 (octet).

Comparative Example A

Preparation of Bis(3,5-bis(trifluoromethyl)phenyl)(2-methoxyphenyl)phosphine, *Ligand 5

This compound is synthesized using the general method shown in Example 2 and isolated at a yield of 15% of the desired product as a clear viscous oil.

1H NMR (C6D6): δ 7.74-7.72 (m, 4H), 7.66-7.65 (m, 2H), 7.04-6.98 (m, 1H), 6.87-6.81 (m, 1H), 6.64-6.58 (m, 1H), 6.35-6.31 (m, 1H), 3.03 (d, 3H, J=1.1); 13C, ppm (C6D6, δ): 161.22 (d), 140.19 (d), 135.01 (d), 133.39 (m), 132.85 (s), 132.38 (d), 131.94 (d), 125.38 (s), 122.98 (m), 121.98 (m), 111.24 (s), 54.82 (s); $^{31}$P NMR (C6D6) δ, (externally referenced with neat H3PO4): −9.26; 19F NMR (C6D6) δ (externally referenced with neat $CCl_3F$): −63.33

Comparative Example B

Catalysts 1-5 are prepared from Ligands 1-5 and evaluated as follows. Preparation of the Precatalyst Stock Solutions:

Pd(acac)$_2$ (0.0294 g, 0.0000966 moles, Aldrich), a phosphine ligand (0.0001932 moles), and acetic acid (0.0000966 moles, 0.50 mL of 0.1932 M HOAc in $CH_3OH$) are dissolved in MeOH to a total volume of 50.00 mL.

Catalytic Telomerization Screening:

To test each ligand, di-n-butyl ether, MeOH, methylcyclohexane, one of the precatalyst stock solutions (1.00 mL), and sodium methoxide (NaOMe) solution (0.5 mL of 0.00193 M NaOMe in MeOH) are syringed into an open Fisher-Porter bottle. Four reactors are run at different methanol concentrations (5.1, 10.4, 12.7, and 14.4 M). 1-3-Butadiene (~3.5 g) is added to the reactors at reaction temperature by gas-tight syringe. Results of the evaluations are shown in Table 1.

activity, measured as percent butadiene conversion over time; in selectivity, to OD-1-R in comparison with OD-3-R and OT; and in stability, measured as turnover number (TON); in comparison with those of the comparative ligands (Ligands 1, 2 and 5).

What is claimed is:

1. A process for the telomerization of butadiene comprising reacting, in a reaction zone in the liquid phase, 1,3-butadiene, and an active hydrogen containing compound, in the presence of a catalyst that comprises a Group VIII transition metal and a phosphine ligand having three phenyl groups, wherein one phenyl group has as a substituent exactly one ortho-alkoxy group, and at least one of the other two phenyl groups comprises at least one substituent that has a Hammett constant value greater than zero, such that the phosphine ligand has a Tolman's chi value ranging from 10 to 18, and a catalyst promoter; under conditions such that a reaction product comprising at least one alkoxy-substituted octadiene is formed.

2. The process of claim 1 wherein the active hydrogen containing compound is an alkanol selected from alcohols having from 1 to 10 carbon atoms.

3. The process of claim 1 or 2 wherein the substituent having a Hammett constant value greater than zero is selected from fluoride, chloride, bromide, iodide, nitro, aldehyde, carboxylic acid, ester, ketone, and cyanide groups; and combinations thereof.

4. The process of any of claims 1 to 3 wherein the phosphine ligand is selected from bis(4-chlorophenyl)(2-methoxy-phenyl)phosphine; bis(4-fluorophenyl)(2-methoxyphenyl)phosphine; and combinations thereof.

5. The process of any of claims 1 to 4 wherein the alkoxy-substituted octadiene is 1-methoxy-2,7-octadiene, and the product further comprises at least one of 1,3,7-octatriene, 3-methoxy octadiene, and combinations thereof.

6. The process of any of claims 1 to 5 wherein the catalyst promoter is selected from tertiary amines, alkali metal borohydrides, oxides, and compounds having a generic formula

TABLE 1

| Catalyst/Ligand | [MeOH] (M/L) | 2 Hr. Bd* Conv. (%) | 4 Hr. Bd Conv. (%) | 4 Hr. TON** (g OD-1-R/g Pd) | OD-1-R Sel. (%) | OD-3-R Sel. (%) | OT Sel. (%) | Linear/branched |
|---|---|---|---|---|---|---|---|---|
| 1(comparative) | 5.1 | 53.4 | 63.6 | 10,640 | 77.9 | 5.3 | 18.1 | 14.7 |
| 1(comparative) | 10.4 | 73.2 | 79.9 | 15,420 | 88.8 | 5.2 | 6.6 | 17.1 |
| 1(comparative) | 12.7 | 71.6 | 83.2 | 16,251 | 89.6 | 4.5 | 6.5 | 19.8 |
| 1(comparative) | 14.4 | 73.1 | 83.3 | 16,385 | 90.3 | 4.6 | 5.2 | 19.6 |
| 2(comparative) | 5.1 | 67.8 | 76.5 | 14,913 | 90.6 | 4.2 | 5.3 | 21.5 |
| 2(comparative) | 10.4 | 70.8 | 78.4 | 16,234 | 93.7 | 3.8 | 2.3 | 25.2 |
| 2(comparative) | 12.7 | 58.8 | 59.9 | 11,574 | 92.6 | 4.0 | 3.1 | 23.1 |
| 2(comparative) | 14.4 | 48.0 | 48.9 | 10,017 | 92.6 | 3.9 | 2.9 | 23.6 |
| 3 | 5.1 | 35.7 | 36.7 | 7,090 | 84.4 | 4.2 | 11.1 | 20.3 |
| 3 | 10.4 | 69.9 | 79.1 | 15,735 | 92.3 | 3.8 | 3.8 | 24.4 |
| 3 | 12.7 | 72.2 | 78.6 | 15,760 | 91.4 | 4.1 | 4.1 | 22.2 |
| 3 | 14.4 | 68.2 | 73.2 | 14,567 | 91.9 | 4.0 | 4.0 | 23.2 |
| 4 | 5.1 | 60.6 | 69.6 | 13,086 | 85.3 | 4.1 | 8.7 | 21.0 |
| 4 | 10.4 | 77.0 | 86.6 | 17,317 | 91.3 | 3.8 | 3.0 | 24.0 |
| 4 | 12.7 | 77.9 | 84.7 | 16,919 | 90.7 | 4.0 | 3.6 | 22.7 |
| 4 | 14.4 | 74.1 | 83.0 | 16,910 | 91.3 | 3.8 | 2.9 | 24.0 |
| 5(comparative) | 5.1 | 2.1 | 2.6 | 162 | 30.9 | 1.9 | 48.6 | 15.9 |
| 5(comparative) | 10.4 | 3.6 | 4.9 | 575 | 52.4 | 2.9 | 36.6 | 17.8 |
| 5(comparative) | 12.7 | 5.6 | 9.9 | 1,227 | 57.2 | 3.4 | 29.0 | 17.0 |

*Bd = Butadiene
**TON = turnover number (g OD-1-R/g Pd)

At comparable methanol concentrations, the example ligands (Ligands 3 and 4) shows general improvements, in ratios of linear (OD-1-R) to branched (OD-3-R) products; in $(RO^-)_n M^{n+}$, wherein R is hydrogen, a $C_1$-$C_{20}$ hydrocarbyl, or a substituted $C_1$-$C_{20}$ hydrocarbyl, M is an alkali metal, alkaline earth metal or quaternary ammonium, and n is 1 or 2.

7. The process of any of claims 1 to 6 further comprising separating at least a portion of the 1-methoxy octadiene from the product and then subjecting the portion of the 1-methoxy octadiene to a hydrogenation reaction and an elimination reaction to form 1-octene.

8. A process for producing 1-octene from butadiene, comprising (1) reacting 1,3-butadiene and an active hydrogen containing compound, in the presence of an alkoxydimerization catalyst comprising a Group VIII transition metal and a phosphine ligand having three phenyl groups, wherein one phenyl group has as a substituent exactly one ortho-alkoxy group, and at least one of the other two phenyl groups comprises at least one substituent that has a Hammett constant value greater than zero, such that the phosphine ligand has a Tolman's chi value ranging from 10 to 18, and a catalyst promoter; under conditions suitable to form an alkoxy-substituted octadiene; (2) hydrogenating the alkoxy-substituted octadiene under conditions suitable to form an alkoxy-substituted octane; and (3) decomposing the alkoxy substituted octane under conditions suitable to form 1-octene.

9. The process of claim 8 wherein the substituent having a Hammett constant value greater than zero is selected from fluoride, chloride, bromide, iodide, nitro, aldehyde, carboxylic acid, ester, ketone, and cyanide groups; and combinations thereof.

* * * * *